（12）United States Patent
Zhang et al.

(10) Patent No.: US 10,167,301 B2
(45) Date of Patent: Jan. 1, 2019

(54) PROCESS FOR THE PREPARATION OF BIS(CHLOROMETHYL)DICHLOROSILANE AND BIS(CHLOROMETHYL)(ARYL)CHLOROSILANE

(71) Applicant: Dow Global Technologies LLC, Midland, MI (US)

(72) Inventors: Chunming Zhang, Midland, MI (US); Heqi Pan, Midland, MI (US); Jerzy Klosin, Midland, MI (US); Philip Fontaine, Lake Jackson, TX (US); David Wilson, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/575,083

(22) PCT Filed: May 25, 2016

(86) PCT No.: PCT/US2016/033983
§ 371 (c)(1),
(2) Date: Nov. 17, 2017

(87) PCT Pub. No.: WO2016/191441
PCT Pub. Date: Dec. 1, 2016

(65) Prior Publication Data
US 2018/0155369 A1 Jun. 7, 2018

Related U.S. Application Data

(60) Provisional application No. 62/166,724, filed on May 27, 2015.

(51) Int. Cl.
*C07F 7/12* (2006.01)
(52) U.S. Cl.
CPC .................... *C07F 7/123* (2013.01)

(58) Field of Classification Search
None
See application file for complete search history.

(56) References Cited

PUBLICATIONS

Daiss et al., Organometallics (2004), 23(22), 5193-5197. (Year: 2004).*
Anderson et al., "Synthesis, Antitumor Activity, and Chemical Properties of Silaplatin and related Platinum (II) and Platinum (IV) Complexes Derived from B-Silyl Amines", J. Med. Chem., 1995, 38, 3789-3797.
Daiss et al., "Synthesis of the Multifunctional (Chloromethyl)silanes Cl2Si(CH2Cl)2, (MeO)2Si(CH2Cl)2, RSi(CH2Cl)3 (R=2,4,6-Trimethoxyphenyl), ClSi(CH2Cl)3, MeOSi(CH2Cl)3, Si(CH2Cl1)4, and ClCH2CH2Si(CH2Cl)3", Organometallics, 2004, 23, 5193-5197.
International Search Report and Written Opinion pertaining to PCT/US2016/033983 dated Jul. 19, 2016.

* cited by examiner

*Primary Examiner* — Clinton A Brooks
*Assistant Examiner* — Kofi Adzamli
(74) *Attorney, Agent, or Firm* — Dinsmore & Shohl LLP

(57) ABSTRACT

The instant invention provides a process for the preparation of bis(chloromethyl)dichlorosilane (BCMCS) or bis(chloromethyl) (aryl)chlorosilane (BCMACS) comprising reacting bis(chloromethyl) diphenylsilane and one or more chloride compounds in the presence of a Lewis acid in an inert solvent and under an inert atmosphere.

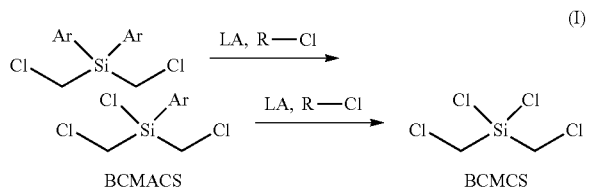

18 Claims, 7 Drawing Sheets

PROCESS FOR THE PREPARATION OF BIS(CHLOROMETHYL)DICHLOROSILANE AND BIS(CHLOROMETHYL)(ARYL)CHLOROSILANE

FIELD OF INVENTION

The instant invention relates to a process for the preparation of bis(chloromethyl)dichlorosilane (BCMCS) and bis(chloromethyl)(aryl)chlorosilane (BCMACS).

BACKGROUND OF THE INVENTION

Bis(chloromethyl)dichlorosilane (BCMCS) and bis(chloromethyl)(aryl)chlorosilane (BCMACS) are versatile starting materials in synthetic organosilicon chemistry with broad applications in advanced silicon materials and pharmaceuticals. They are also key building blocks for preparation of advanced silicon-containing catalysts for olefin polymerizations. Unfortunately, there has been no practical method to prepare these important materials. The currently known preparation methods for BCMCS include the following methods shown below:

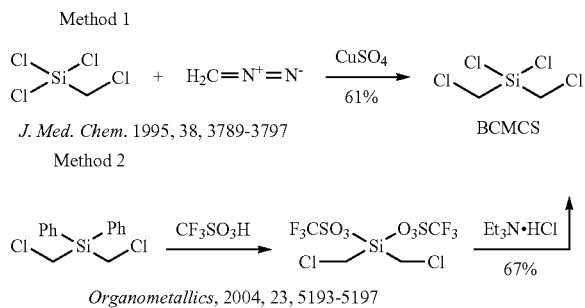

The currently known preparation methods for BCMACS, wherein the aryl group is phenyl, include the following method shown below:

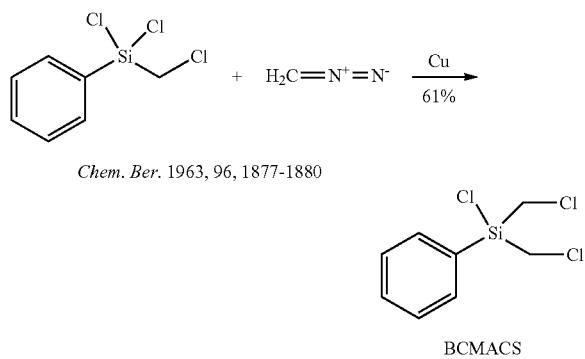

The currently known preparation methods for BCMCS or BCMACS either require dangerous chemistry (diazomethane), or utilize expensive strong acids while generating highly toxic byproducts (benzene, in the case of Ar=phenyl), and low yields.

Accordingly, there is a need for an improved and practical method for preparation of bis(chloromethyl)dichlorosilane and bis(chloromethyl)(aryl)chlorosilane in high yield safely at a relatively low cost.

SUMMARY OF THE INVENTION

The instant invention provides a process for the preparation of bis(chloromethyl)dichlorosilane (BCMCS) and bis(chloromethyl)(aryl)chlorosilane (BCMACS) comprising contacting bis(chloromethyl)diarylsilane and one or more chloride compounds in the presence of one or more Lewis acids in an inert solvent and under an inert atmosphere. Further provided is a process for the preparation of bis(chloromethyl)dichlorosilane (BCMCS) comprising contacting bis(chloromethyl)(aryl)chlorosilane (BCMACS) and one or more chloride compounds in the presence of one or more Lewis acids in an inert solvent and under an inert atmosphere.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

Figure 1:
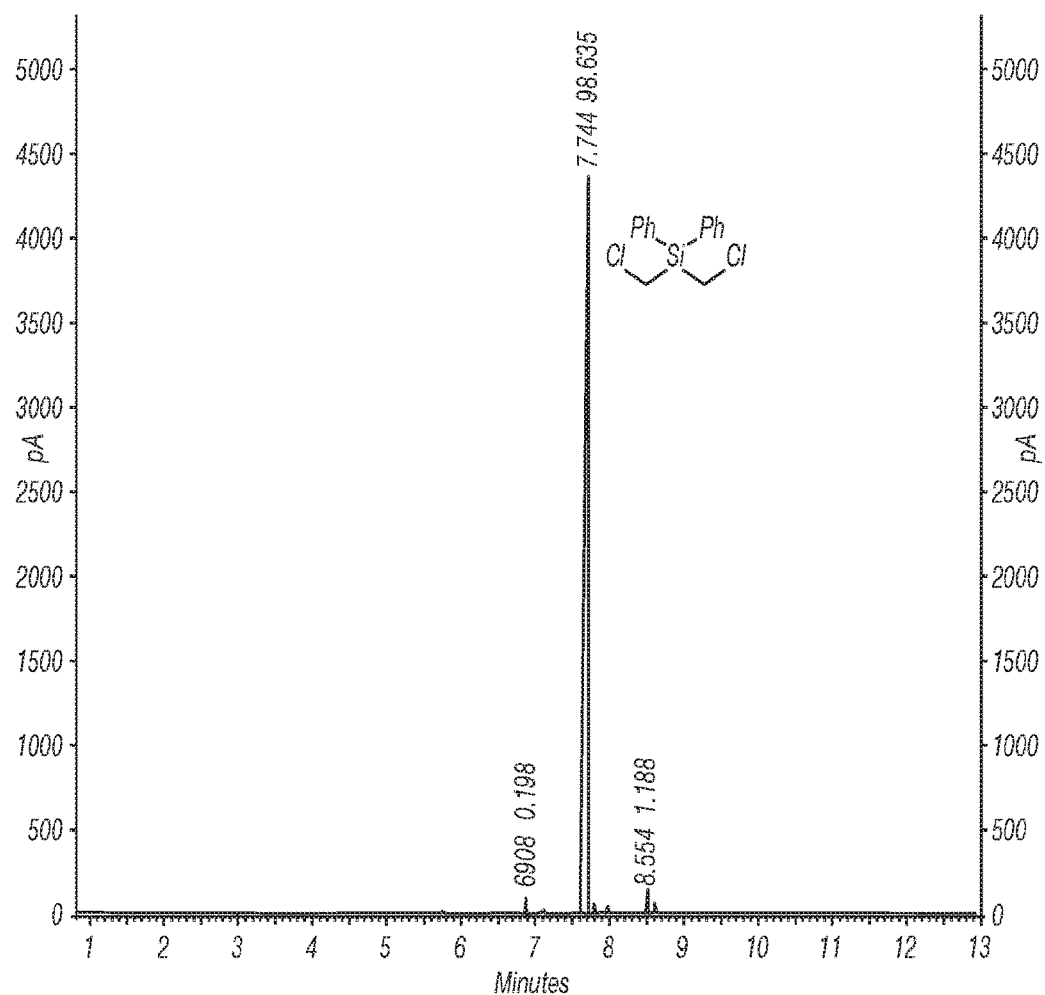
FIG. 1 is a GC spectra of starting material bis(chloromethyl)diphenylsilane according to Examples 1 and 2.
Figure 2:
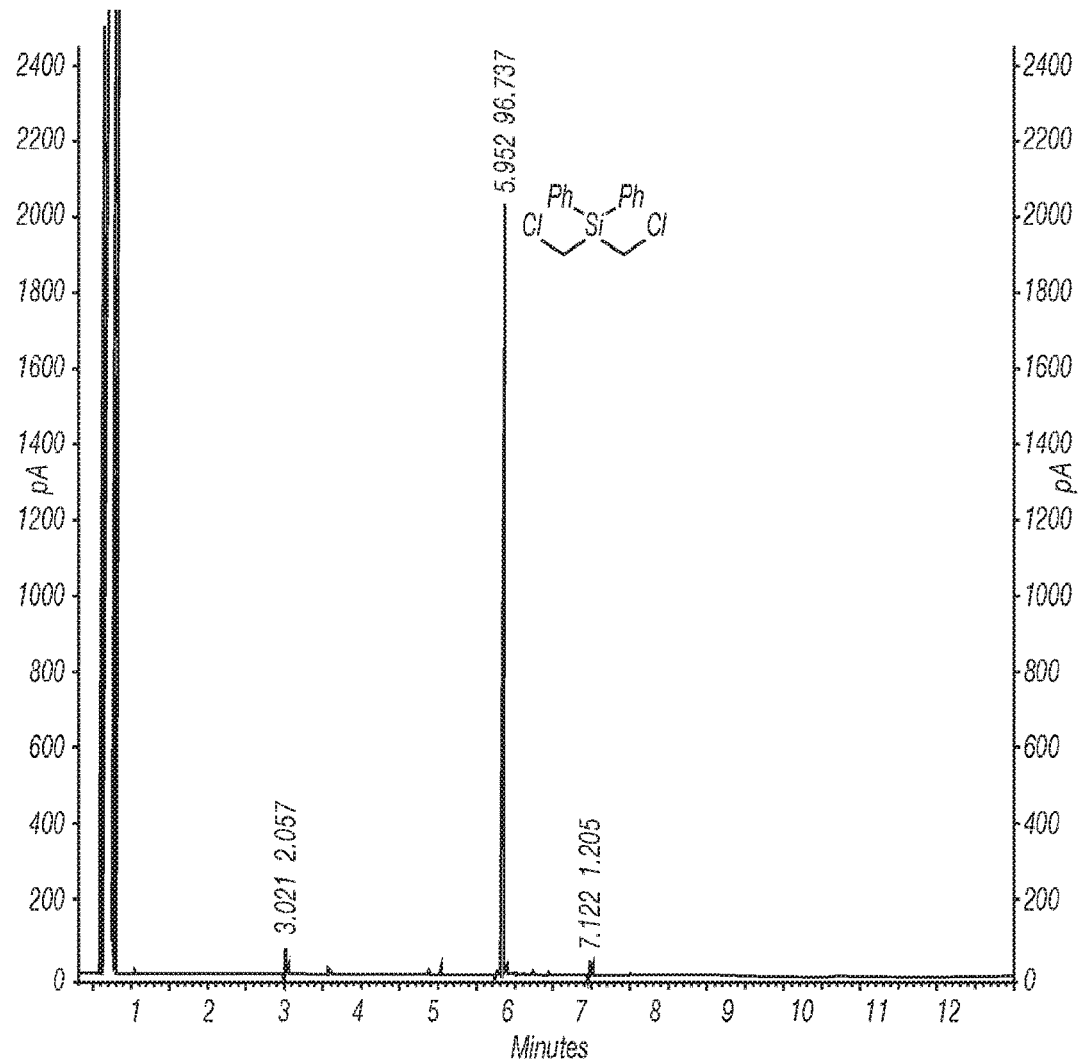
FIG. 2 is a GC spectra of crude bis(chloromethyl)(phenyl)chlorosilane according to Example 1.
Figure 3:
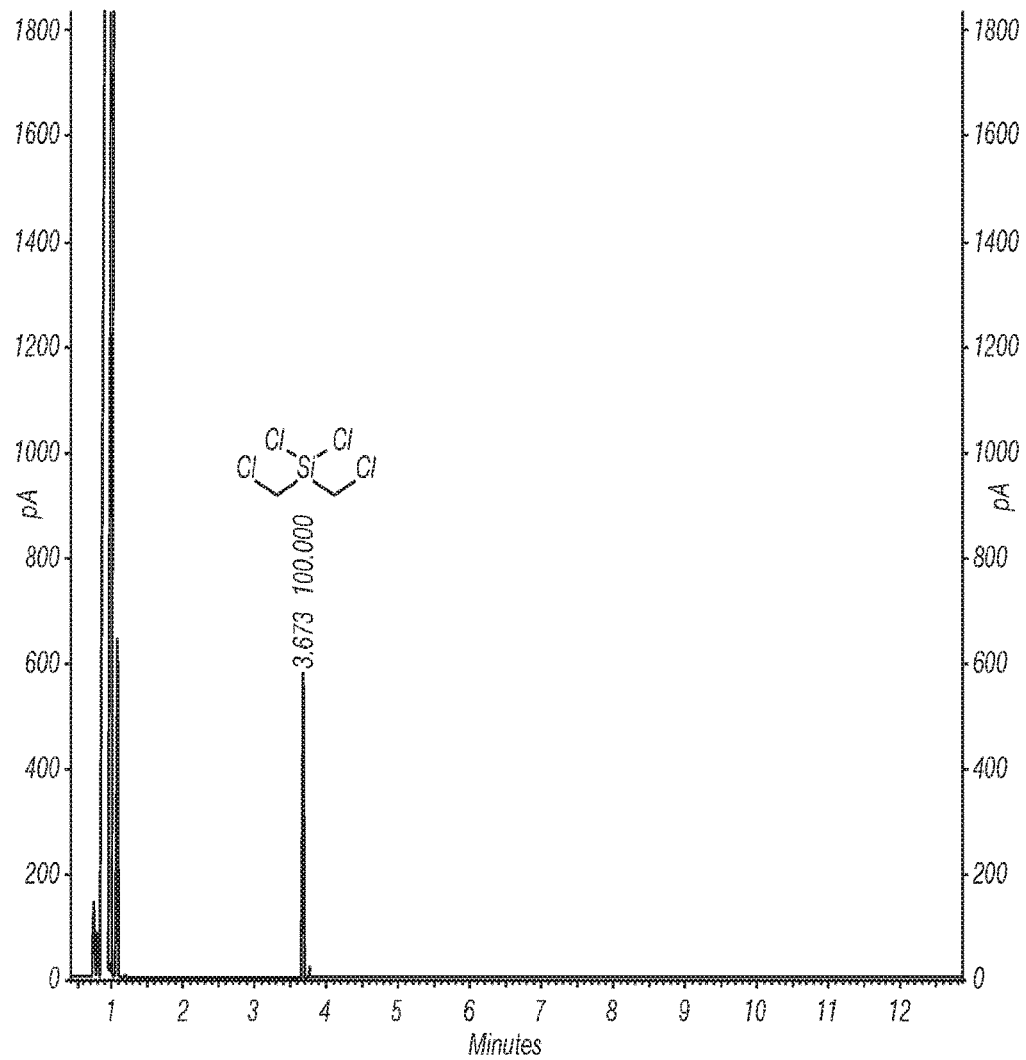
FIG. 3 is a GC spectra of bis(chloromethyl)dichlorosilane according to Example 2.
Figure 4:
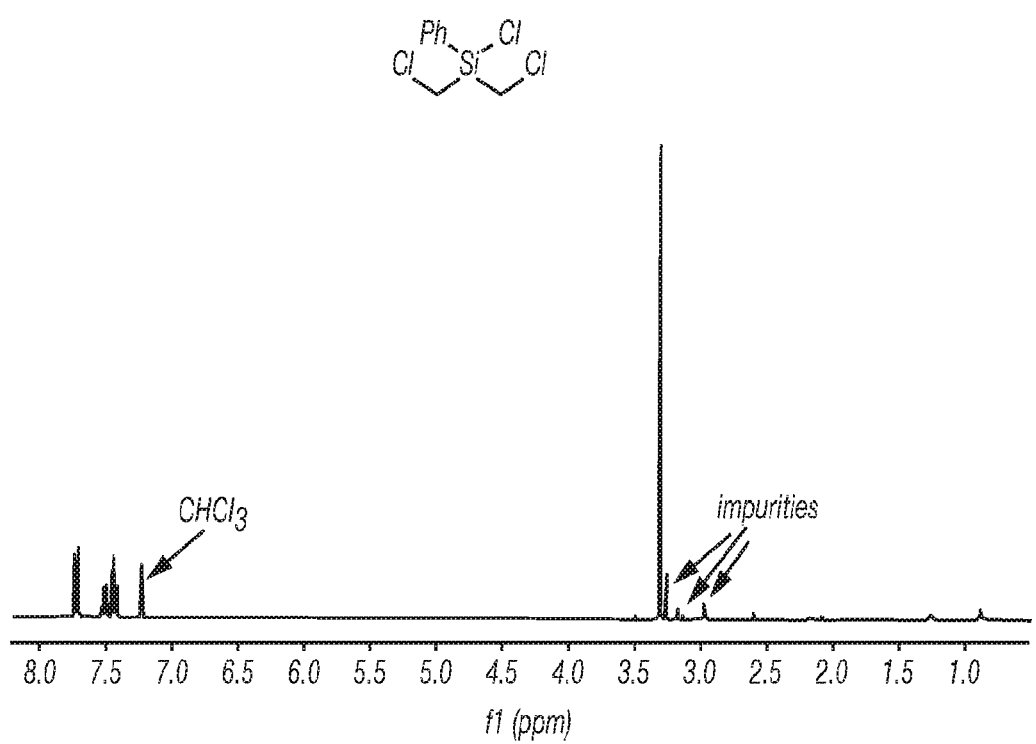
FIG. 4 is an $^1$H NMR spectra of crude bis(chloromethyl)(phenyl)chlorosilane (CDCl$_3$, 400 MHz) according to Example 1.
Figure 5:
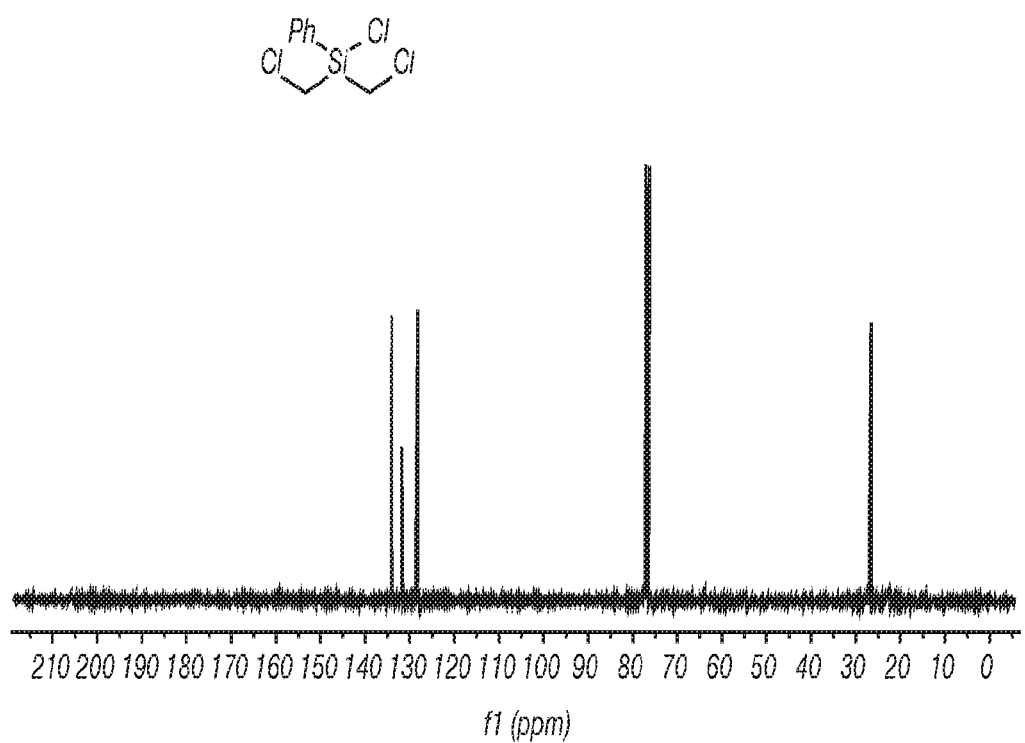
FIG. 5 is an $^{13}$C NMR spectra of crude bis(chloromethyl)(phenyl)chlorosilane (CDCl$_3$, 101 MHz) according to Example 1.
Figure 6:
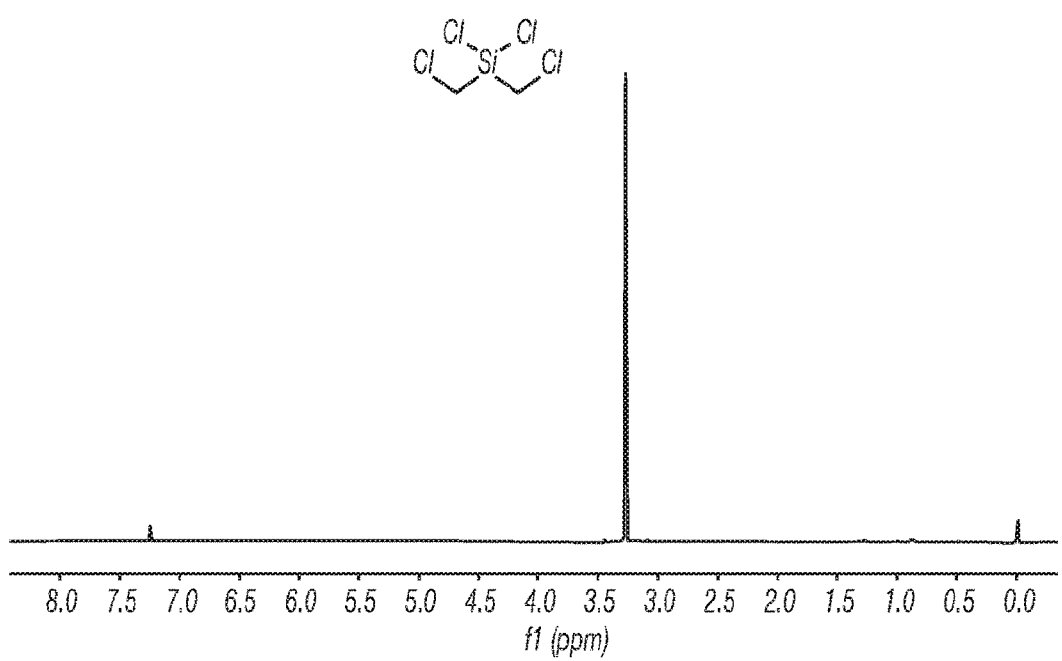
FIG. 6 is an $^1$H NMR spectra of bis(chloromethyl)dichlorosilane (CDCl$_3$, 400 MHz) according to Example 2.
Figure 7:
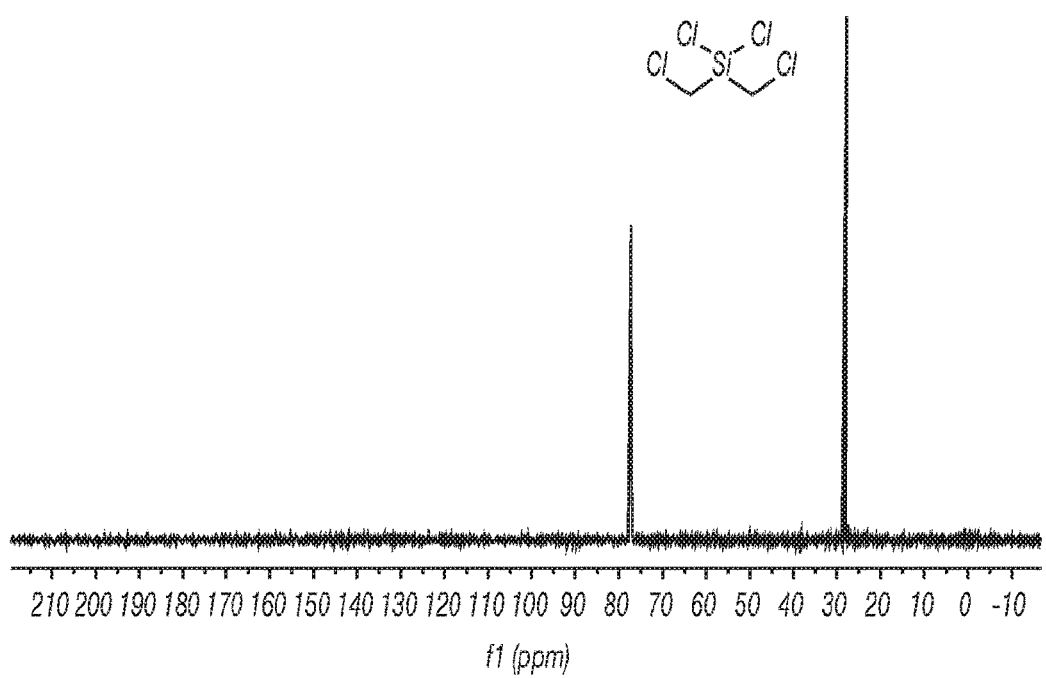
FIG. 7 is an $^{13}$C NMR spectra of bis(chloromethyl)dichlorosilane (CDCl$_3$, 101 MHz) according to Example 2.

In the process of the instant invention, bis(chloromethyl)(aryl)chlorosilane (BCMACS) may be considered to be an intermediate product in the process to prepare bis(chloromethyl)dichlorosilane BCMCS from bis(chloromethyl)diarylsilane. Accordingly, the process of the invention to prepare BCMCS may start from bis(chloromethyl)diarylsilane or from BCMACS. The process of the invention to prepare BCMACS may be carried out in a similar manner by starting from bis(chloromethyl)diarylsilane with the proviso that the process is stopped at the BCMACS stage, that is, when the desired level of conversion to BCMACS has been attained.

The instant invention provides a process for the preparation of BCMCS and/or BCMACS comprising contacting bis(chloromethyl)diarylsilane and one or more chloride compounds in the presence of one or more Lewis acids in an inert solvent and under an inert atmosphere. The instant invention also provides a process for the preparation of BCMACS comprising contacting bis(chloromethyl)diarylsilane and one or more chloride compounds in the presence of one or more Lewis acids in an inert solvent and under an inert atmosphere. The process for the preparation of BCMCS and/or BCMACS according to the present invention can be represented by the following:

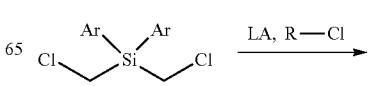

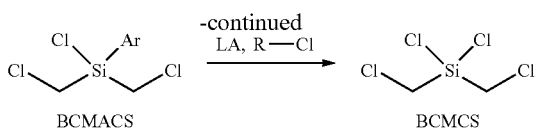

BCMACS → BCMCS wherein Ar independently selected is an aryl group; R—Cl is a chloride compound; LA is a Lewis acid The one or more chloride compounds can be any suitable chloride compound; for example the one or more chloride compounds can be selected from the group consisting of acid chlorides (also known as acyl chlorides), chloroformates, sulfonyl chlorides, thionyl chloride, hydrocarbyl chlorides, and heterohydrocarbyl chlorides. In an alternative embodiment, the one or more chloride compounds may comprise a mixture of chloride compounds wherein the mixture of chloride compounds comprises chloride compounds selected from at least two different members of the group consisting of acid chlorides, chloroformates, sulfonyl chlorides, thionyl chloride, hydrocarbyl chlorides, and heterohydrocarbyl chlorides.

Preferred acid chlorides have from one to twenty carbon atoms, preferably from one to ten carbon atoms, more preferably from one to seven carbon atoms. Preferred acid chlorides may be selected from the group consisting of acetyl chloride, propionyl chloride, butanoyl chloride, pentanoyl chloride, hexanoyl chloride, benzoyl chloride, acryloyl chloride, methacryloyl chloride, oxalyl chloride, malonyl chloride, succinoyl chloride, glutaroyl chloride, adipoyl chloride, pimeloyl chloride, dichloroacetyl chloride, and trichloroacetyl chloride. More preferred acid chlorides may be selected from the group consisting of acetyl chloride, propionyl chloride, butanoyl chloride, benzoyl chloride, acryloyl chloride, methacryloyl chloride, oxalyl chloride, malonyl chloride, succinoyl chloride, and adipoyl chloride. Even more preferred acid chlorides may be selected from the group consisting of acetyl chloride, propionyl chloride, and oxalyl chloride. The most preferred acid chloride is acetyl chloride.

Preferred chloroformates have from one to twenty carbon atoms, preferably from one to ten carbon atoms, more preferably from one to seven carbon atoms. Preferred chloroformates may be selected from the group consisting of methyl chloroformate, ethyl chloroformate, propyl chloroformate, isopropyl chloroformate, butyl chloroformate, isobutyl chloroformate, ethylenebis(chloroformate), phenyl chloroformate, and benzyl chloroformate. More preferred chloroformates may be selected from the group consisting of methyl chloroformate, ethyl chloroformate, propyl chloroformate, isopropyl chloroformate, butyl chloroformate, and isobutyl chloroformate. Most preferred chloroformates may be selected from the group consisting of methyl chloroformate, ethyl chloroformate, propyl chloroformate, and isopropyl chloroformate.

Preferred sulfonyl chlorides have from one to twenty carbon atoms, preferably from one to ten carbon atoms, more preferably from one to seven carbon atoms. Preferred sulfonyl chlorides may be selected from the group consisting of methanesulfonyl chloride, ethanesulfonyl chloride, propanesulfonyl chloride, butanesulfonyl chloride, benzenesulfonyl chloride, toluenesulfonyl chloride. More preferred sulfonyl chlorides may be selected from the group consisting of methanesulfonyl chloride, ethanesulfonyl chloride, and toluenesulfonyl chloride.

Preferred hydrocarbyl chlorides have from one to twenty carbon atoms, preferably from one to ten carbon atoms, more preferably from one to seven carbon atoms. Preferred hydrocarbyl chlorides may be selected from the group consisting of chloropropane, chlorobutane, dichloromethane, dichloroethane, chloroform, trichloroethane, tetrachloroethane, allyl chloride, benzyl chloride.

Preferred heterohydrocarbyl chlorides have from one to twenty carbon atoms, preferably from one to ten carbon atoms, more preferably from one to seven carbon atoms. Preferred heterohydrocarbyl chlorides may be selected from the group consisting of 1-chloropyridinium chloride, 4-methoxybenzyl chloride, imidazolium chloride, 2-chloromethylpyridine, 4-chloromethylpyridine.

In an alternative embodiment, the one or more chloride compounds may comprise a mixture of at least two chloride compounds selected from the group consisting of acetyl chloride, propionyl chloride, methyl chloroformate, ethyl chloroformate, methanesulfonyl chloride, ethanesulfonyl chloride, toluenesulfonyl chloride, dichloromethane, chloroform, 2-chloromethylpyridine, 4-methoxybenzyl chloride, and thionyl chloride.

The term "aryl group" is defined as in the IUPAC Goldbook (IUPAC: International Union of Pure and Applied Chemistry, http://goldbook.iupac.org/A00464.html), that is, groups derived from monoyclic and polycyclic aromatic hydrocarbons by removal of a hydrogen atom from a ring carbon atom. Aryl groups of the bis(chloromethyl)diarylsilane and bis(chloromethyl)(aryl)chlorosilane independently selected can be any suitable aryl group having from 6 to 20 carbon atoms, preferably 6 to 12 carbon atoms, more preferably 6 to 8 carbon atoms. In one embodiment the aryl groups are different from each other. In another embodiment the aryl groups are the same. Preferably the aryl groups are independently selected from the group consisting of phenyl, tolyl, xylyl, mesityl, naphthyl, biphenyl, anthracenyl; more preferably the aryl groups are selected from the group consisting of phenyl, tolyl, xylyl; more preferably at least one aryl group is phenyl, still more preferably all of the aryl groups are phenyl. In the most preferred embodiment, the bis(chloromethyl)diarylsilane is bis(chloromethyl)diphenylsilane and the bis(chloromethyl)(aryl)chlorosilane is bis(chloromethyl)(phenyl)chlorosilane.

The one or more Lewis acids can be any Lewis acid; preferably the one or more Lewis acids comprises chloride. The one or more Lewis acids can comprise a mixture of Lewis acids. Preferably the one or more Lewis acids can be selected from the group consisting of boron chloride, aluminum chloride, zinc chloride, magnesium chloride, zirconium chloride, hafnium chloride, and titanium chloride. More preferably, the Lewis acid is aluminum chloride.

The inert solvent can be any solvent; for example, the inert solvent can be one or more hydrocarbon solvents or chlorinated hydrocarbon solvents. In an alternative embodiment, the one or more hydrocarbon solvents are selected from the group consisting of saturated aliphatic hydrocarbons. In another alternative embodiment, the one or more hydrocarbon solvents are selected from the group consisting of pentane, hexane, heptane, and octane. In another alternative embodiment, the one or more hydrocarbon solvents are selected from the group consisting of isoparaffins. Such one or more hydrocarbon solvents can have a boiling point in the range of from 20 to 200° C. In an alternative embodiment, the one or more chlorinated hydrocarbon solvents are selected from the group consisting of dichloromethane, chloroform, chlorobenzene, dichlorobenzene, dichloroethane, trichloroethane, tetrachloroethane, and tetrachloroethylene.

In the inventive process for the preparation of BCMCS and/or BCMACS, the inert atmosphere can, for example, be provided by flushing with an inert gas. Such inert gases include, but are not limited to, nitrogen and/or argon gas.

In inventive process for the preparation of BCMCS and/or BCMACS, the ratio of the at least one chloride compound to the bis(chloromethyl)diarylsilane may range from 1:100 to 100:1, preferably from 1:10 to 50:1, more preferably from 1:1 to 20:1, even more preferably from 1.5:1 to 10:1, still more preferably from 2:1 to 5:1.

The process for the preparation of BCMCS and/or BCMACS according to the present invention can be carried out at a process temperature in the range of from −80° C. to 100° C. In one embodiment, the process can be carried out at a temperature in the range of from −30° C. to 50° C. In an alternative embodiment, the process can be carried out at a temperature in the range of from −20° C. to 40° C. In an alternative embodiment, the process can be carried out at a temperature in the range of from −10° C. to 40° C. In an alternative embodiment, the process can be carried out at a temperature in the range from −10° C. to 35° C. In an alternative embodiment, the process can be carried out at a temperature in the range from −10° C. to 10° C. In an alternative embodiment, the process can be carried out stepwise with respect to the temperature, wherein the process is carried out in an initial first temperature range and then optionally in an at least one additional temperature range. Preferably the initial first temperature range is lower than the at least one additional temperature range. Preferably the initial temperature is in the range from −20° C. to 20° C., more preferably from −10° C. to 10° C., even more preferably at or near 0° C., that is, at ice bath temperature. Preferably the temperature of at least part of the process is attained with use of an ice bath. Preferably the at least one additional temperature is in the range of 0° C. to 40° C. Preferred temperature ranges, including first initial temperature ranges and optional additional temperature ranges include from −30° C. to 50° C., −20° C. to 40° C., −10° C. to 40° C., −10° C. to 35° C., −20° C. to 20° C., −10° C. to 10° C., −5° C. to 5° C., at or near 0° C., that is, at ice bath temperature, 10° C. to 40° C., 15° C. to 35° C., 20° C. to 25° C., 25° C. to 30° C., 30° C. to 35° C.

According to the present invention a process is provided whereby the preparation of either BCMCS or BCMACS may be selected by choice of the reaction conditions. The preparation of BCMACS may be favored by employing a lower ratio of the at least one chloride compound to the bis(chloromethyl)diarylsilane, preferably in a range from 1:10 to 3:1, more preferably in a range from 1:1.1 to 2.5:1, most preferably in a range from 1:1.1 to 1.5:1, while the preparation of BCMCS may be favored by employing a higher ratio of the at least one chloride compound to the bis(chloromethyl)diarylsilane, preferably in a range from 1:1 to 10:1, more preferably in a range from 1.5:1 to 5:1, most preferably in a range from 2:1 to 2.5:1. The preparation of BCMACS may be favored by selection of a lower temperature range for carrying out the process. Without wishing to be bound by belief, it is believed that carrying out the process in an initial lower first temperature range allows for the first aryl group to be replaced by chloride to give BCMACS at a rate such that good conversion to BCMACS occurs without substantial further conversion to BCMCS occurring, while further carrying out the process in an optional higher temperature range results in conversion of BCMACS to BCMCS.

The process for the preparation of BCMCS and/or BCMACS according to the present invention can produce BCMCS and/or BCMACS in high yield, for example, at least 80% yield, or at least 90% yield. In an alternative embodiment, the instant invention provides a process for the preparation of BCMCS and/or BCMACS according to any embodiment described herein, except that the process produces BCMCS and/or BCMACS in yields equal to or less than 100%; or in the alternative, equal to or less than 95%. Yields are based on moles of reactants.

In an alternative embodiment, the instant invention provides a process for the preparation of BCMCS and/or BCMACS, in accordance with any embodiment described herein, except that one or more chloride compounds are selected from the group consisting of acid chlorides, chloroformates, sulfonyl chlorides, and thionyl chloride.

In an alternative embodiment, the instant invention provides a process for the preparation of BCMCS and/or BCMACS, in accordance with any embodiment described herein, except that the one or more chloride compounds are selected from the group consisting of hydrocarbyl chlorides and heterohydrocarbyl chlorides.

In an alternative embodiment, the instant invention provides a process for the preparation of BCMCS and/or BCMACS, in accordance with any embodiment described herein, except that the one or more chloride compounds are selected from the group consisting of acetyl chloride, propionyl chloride and oxalyl chloride.

In an alternative embodiment, the instant invention provides a process for the preparation of BCMCS and/or BCMACS, in accordance with any embodiment described herein, except that the one or more chloride compounds is selected from the group consisting of methyl chloroformate, ethyl chloroformate, benzyl chloroformate, and isobutyl chloroformate.

In an alternative embodiment, the instant invention provides a process for the preparation of BCMCS and/or BCMACS, in accordance with any embodiment described herein, except that the one or more acid chlorides is acetyl chloride.

In an alternative embodiment, the instant invention provides a process for the preparation of BCMCS and/or BCMACS, in accordance with any embodiment described herein, except that the one or more Lewis acids is selected from the group consisting of boron chloride, aluminum chloride, zinc chloride, magnesium chloride, zirconium chloride, hafnium chloride, and titanium chloride.

In an alternative embodiment, the instant invention provides a process for the preparation of BCMCS and/or BCMACS, in accordance with any embodiment described herein, except that the Lewis acid is aluminum chloride.

In an alternative embodiment, the instant invention provides a process for the preparation of BCMCS and/or BCMACS, in accordance with any embodiment described herein, except that the inert solvent is one or more hydrocarbon solvents.

In an alternative embodiment, the instant invention provides a process for the preparation of BCMCS and/or BCMACS, in accordance with any embodiment described herein, except that the one or more hydrocarbon solvents are selected from the group consisting of saturated aliphatic hydrocarbons.

In an alternative embodiment, the instant invention provides a process for the preparation of BCMCS and/or BCMACS, in accordance with any embodiment described herein, except that the one or more hydrocarbon solvents are selected from the group consisting of pentane, hexane, heptane, and octane.

In an alternative embodiment, the instant invention provides a process for the preparation of BCMCS and/or BCMACS, in accordance with any embodiment described herein, except that the one or more hydrocarbon solvents are selected from the group consisting of isoparaffins.

In an alternative embodiment, the instant invention provides a process for the preparation of BCMCS and/or BCMACS, in accordance with any embodiment described herein, except that the one or more hydrocarbon solvents have a boiling point from 20 to 200° C.

In an alternative embodiment, the instant invention provides a process for the preparation of BCMCS and/or BCMACS, in accordance with any embodiment described herein, except that the inert atmosphere is provided by flushing with an inert gas.

In an alternative embodiment, the instant invention provides a process for the preparation of BCMCS and/or BCMACS, in accordance with any embodiment described herein, except that the inert atmosphere is provided by lowering the pressure to from 0.001 Torr to 100 Torr, preferably from 0.001 Torr to 10 Torr, more preferably from 0.001 Torr to 1.0 Torr, most preferably from 0.001 Torr to 0.1 Torr, and substantially restoring the pressure by refilling with an inert gas. Preferably the process of lowering and restoring the pressure may be carried out at least one time, preferably from one to four times.

In an alternative embodiment, the instant invention provides a process for the preparation of BCMCS and/or BCMACS, in accordance with any embodiment described herein, except that the inert gas is nitrogen and/or argon gas.

In an alternative embodiment, the instant invention provides a process for the preparation of BCMCS and/or BCMACS, in accordance with any embodiment described herein, except that the process further comprises heating the reaction mixture to a temperature from −30° C. to 100° C.

In an alternative embodiment, the instant invention provides a process for the preparation of BCMCS and/or BCMACS, in accordance with any embodiment described herein, except that the reacting occurs at a temperature from −10° C. to 50° C.

In an alternative embodiment, the instant invention provides a process for the preparation of BCMCS and/or BCMACS, in accordance with any embodiment described herein, except that the reacting occurs at a temperature from 0° C. to 30° C.

In an alternative embodiment, the instant invention provides a process for the preparation of BCMCS and/or BCMACS, in accordance with any embodiment described herein, wherein the yield of BCMCS and/or BCMACS based on the molar amount of bis(chloromethyl)diarylsilane used is 50% or greater, preferably 75% or greater, more preferably 90% or greater.

In an alternative embodiment, the instant invention provides a process for the preparation of BCMCS, in accordance with any embodiment described herein, except that the process comprises contacting bis(chloromethyl)diphenylsilane, acetyl chloride, and aluminum chloride, as represented:

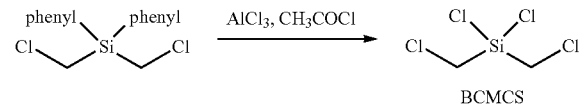

BCMCS

In an alternative embodiment, the instant invention provides a process for the preparation of bis(chloromethyl)(phenyl)chlorosilane, in accordance with any embodiment described herein, except that the process comprises contacting bis(chloromethyl)diphenylsilane, acetyl chloride, and aluminum chloride, as represented:

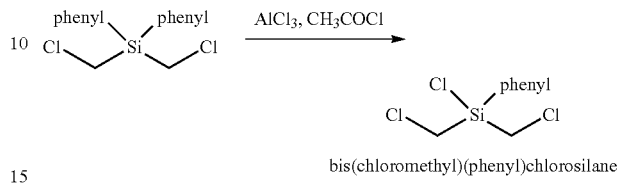

bis(chloromethyl)(phenyl)chlorosilane

EXAMPLES

The following examples illustrate the present invention but are not intended to limit the scope of the invention. The examples of the instant invention demonstrate that the process for the preparation of BCMCS and/or BCMACS according to the present invention can produce BCMCS and/or BCMACS safely at low cost while generating high yield.

Inventive Example 1

Inventive Example 1 was prepared according to the following procedure. A 1-L three-neck round-bottom flask equipped with an overhead stirrer, a thermometer, and a nitrogen pad was charged with $AlCl_3$ (33.5 g, 250 mmol) and anhydrous hexane (450 mL). The reaction mixture was cooled to near or at 0° C. in an ice bath, and bis(chloromethyl)diphenylsilane (28.1 g, 100 mmol) was added at 0° C., followed by addition of acetyl chloride (18 mL, 250 mmol) in hexane (50 mL) in an ice bath. The reaction mixture was allowed to stir in an ice bath for 4 h. A sample was taken for $^1H$ NMR analysis, which indicated the formation of the intermediate $(ClCH_2)_2Si(Ph)Cl$ as the only product. The reaction mixture was warmed up to ambient temperature and stirred until all the $(ClCH_2)Si(Ph)Cl$ was converted to the desired product $(ClCH_2)_2SiCl_2$ (overnight). The resulting reaction mixture was filtered under a nitrogen atmosphere. The wet-cake was rinsed with dry hexane (100 mL). Concentration of the filtrate under reduced pressure gave the desired product, $(ClCH_2)_2SiCl_2$, 17.5 g (88% yield).

Inventive Example 2

Inventive Example 2 was prepared according to the following procedure. A 2-L 3-neck round-bottom flask equipped with an overhead stirrer, a thermometer, and a nitrogen pad, was charged with $AlCl_3$ (105.5 g, 791.2 mmol) and anhydrous hexane (900 mL). The reaction flask was cooled in a cold water bath and bis(chloromethyl)diphenylsilane (89.02 g, 316.5 mmol) was added at 20° C. Upon completion of addition of bis(chloromethyl)diphenylsilane (20 min), acetyl chloride (56.2 mL, 791.2 mmol) was added through a syringe pump over 3 hours at 20° C. The reaction mixture was stirred at 20-25° C. overnight, and then warmed up to 30-35° C. until the reaction was complete (3 hours) as monitored by $^1H$ NMR. The reaction mixture was cooled to ambient temperature and filtered under a nitrogen atmosphere. The solid was washed with hexane (3×100 mL). The filtrate was concentrated with a rotary evaporator under reduced pressure to give the desired product, $(ClCH_2)_2SiCl_2$, 56.46 g (90% yield).

Test Methods

Test methods include Nuclear Magnetic Resonance (NMR) and gas chromatography (GC). NMR spectra were recorded on a Bruker 400 (FT 400 MHz, 1H; 101 MHz, 13C) spectrometer.

Gas chromatography was conducted on an AGILENT 7890A gas chromatograph with an auto sampler using the following conditions:
Column: 15 m×0.32 mm×0.25 μm DB-5
Column Temperature 100-320° C.
Injector: Split/Splitless 50:1 ratio; Split flow 95.074 mL/min
320° C.
Detector: Flame Ionization
300° C.
Oven program: 100° C. for 2 min then 30° C./min to 320° C. for 3 min;
Run time 13 min
Injection: 1 μL The present invention may be embodied in other forms without departing from the spirit and the essential attributes thereof, and, accordingly, reference should be made to the appended claims, rather than to the foregoing specification, as indicating the scope of the invention.

We claim:

1. A process for the preparation of bis(chloromethyl)dichlorosilane comprising reacting bis(chloromethyl)diarylsilane and one or more chloride compounds in the presence of one or more Lewis acids in an inert solvent and under an inert atmosphere.

2. The process of claim 1, wherein the aryl of the bis(chloromethyl)diarylsilane is independently selected from the group consisting of phenyl, tolyl, xylyl, mesityl, naphthyl, biphenyl, and anthracenyl.

3. The process of claim 1, wherein the one or more chloride compounds are selected from the group consisting of acid chlorides, chloroformates, sulfonyl chlorides, thionyl chloride, hydrocarbyl chlorides, and heterohydrocarbyl chlorides.

4. The process of claim 1, wherein the one or more Lewis acids are selected from the group consisting of boron chloride, aluminum chloride, zinc chloride, magnesium chloride, zirconium chloride, hafnium chloride, and titanium chloride.

5. The process of claim 1, wherein the inert solvent comprises one or more hydrocarbon solvents selected from the group consisting of pentane, hexane, heptane, octane, dichloromethane, chloroform, chlorobenzene, dichlorobenzene, dichloroethane, trichloroethane, tetrachloroethane, and tetrachloroethylene.

6. The process of claim 1, wherein the process is carried out in an initial first temperature range and in an at least one additional temperature range, wherein the first temperature range is lower than the at least one additional temperature range.

7. A process for the preparation of bis(chloromethyl)(aryl)chlorosilane comprising reacting bis(chloromethyl)diarylsilane and one or more chloride compounds in the presence of one or more Lewis acids in an inert solvent and under an inert atmosphere.

8. The process of claim 7, wherein the aryl is independently selected from the group consisting of phenyl, tolyl, xylyl, mesityl, naphthyl, biphenyl, and anthracenyl.

9. The process of claim 7, wherein the one or more chloride compounds are selected from the group consisting of acid chlorides, chloroformates, sulfonyl chlorides, thionyl chloride, hydrocarbyl chlorides, and heterohydrocarbyl chlorides.

10. The process of claim 7, wherein the one or more Lewis acids are selected from the group consisting of boron chloride, aluminum chloride, zinc chloride, magnesium chloride, zirconium chloride, hafnium chloride, and titanium chloride.

11. The process of claim 7, wherein the inert solvent comprises one or more hydrocarbon solvents selected from the group consisting of pentane, hexane, heptane, octane, dichloromethane, chloroform, chlorobenzene, dichlorobenzene, dichloroethane, trichloroethane, tetrachloroethane, and tetrachloroethylene.

12. The process of claim 7, wherein the process is carried out in an initial first temperature range and in an at least one additional temperature range, wherein the first temperature range is lower than the at least one additional temperature range.

13. A process for the preparation of bis(chloromethyl)dichlorosilane comprising reacting bis(chloromethyl)(aryl)chlorosilane and one or more chloride compounds in the presence of one or more Lewis acids in an inert solvent and under an inert atmosphere.

14. The process of claim 13, wherein the aryl of the bis(chloromethyl)(aryl)chlorosilane is independently selected from the group consisting of phenyl, tolyl, xylyl, mesityl, naphthyl, biphenyl, and anthracenyl.

15. The process of claim 13, wherein the one or more chloride compounds are selected from the group consisting of acid chlorides, chloroformates, sulfonyl chlorides, thionyl chloride, hydrocarbyl chlorides, and heterohydrocarbyl chlorides.

16. The process of claim 13, wherein the one or more Lewis acids are selected from the group consisting of boron chloride, aluminum chloride, zinc chloride, magnesium chloride, zirconium chloride, hafnium chloride, and titanium chloride.

17. The process of claim 13, wherein the inert solvent comprises one or more hydrocarbon solvents selected from the group consisting of pentane, hexane, heptane, octane, dichloromethane, chloroform, chlorobenzene, dichlorobenzene, dichloroethane, trichloroethane, tetrachloroethane, and tetrachloroethylene.

18. The process of claim 13, wherein the process is carried out in an initial first temperature range and in an at least one additional temperature range, wherein the first temperature range is lower than the at least one additional temperature range.

* * * * *